United States Patent
Guo et al.

(10) Patent No.: US 10,705,246 B2
(45) Date of Patent: Jul. 7, 2020

(54) METHOD OF ROCK MINERALOGY INTERPRETATION

(71) Applicants: Pingjun Guo, Bellaire, TX (US); Mathilde M. Luycx, Austin, TX (US)

(72) Inventors: Pingjun Guo, Bellaire, TX (US); Mathilde M. Luycx, Austin, TX (US)

(73) Assignee: ExxonMobil Upstream Research Company, Spring, TX (US)

( * ) Notice: Subject to any disclaimer, the term of this patent is extended or adjusted under 35 U.S.C. 154(b) by 232 days.

(21) Appl. No.: 15/725,341

(22) Filed: Oct. 5, 2017

(65) Prior Publication Data
US 2018/0149768 A1    May 31, 2018

Related U.S. Application Data

(60) Provisional application No. 62/426,921, filed on Nov. 28, 2016.

(51) Int. Cl.
G01V 5/04 (2006.01)
G01N 33/24 (2006.01)
G01V 5/10 (2006.01)

(52) U.S. Cl.
CPC ............ *G01V 5/045* (2013.01); *G01N 33/24* (2013.01); *G01V 5/102* (2013.01)

(58) Field of Classification Search
CPC .................................................. G01V 5/045
See application file for complete search history.

(56) References Cited

U.S. PATENT DOCUMENTS

| | | | | |
|---|---|---|---|---|
| 4,712,424 A | * | 12/1987 | Herron | G01V 11/00 250/256 |
| 4,722,220 A | * | 2/1988 | Herron | G01V 11/00 250/253 |
| 4,903,527 A | * | 2/1990 | Herron | G01V 11/00 702/12 |
| 4,914,944 A | * | 4/1990 | Herron | G01V 11/00 702/13 |
| 8,311,744 B2 | | 11/2012 | Khisamutdinov et al. | |
| 9,310,513 B2 | | 4/2016 | Scoullar et al. | |
| 2007/0246649 A1 | * | 10/2007 | Jacobi | G01V 5/101 250/269.6 |
| 2010/0312479 A1 | * | 12/2010 | Khisamutdinov | E21B 47/1015 702/8 |

(Continued)

OTHER PUBLICATIONS

Colson, J.L., et al. (1989) "Applications Using Geochemical Logs", SPE-17963-MS, the SPE Middle East Oil Show, Manama, Bahrain, Mar. 11-14; pp. 365-372.

(Continued)

*Primary Examiner* — Raymond L Nimox
(74) *Attorney, Agent, or Firm* — ExxonMobil Upstream Research Company—Law Department

(57) ABSTRACT

A method to interpret and quantify mineral compositions and concentrations, the method including: determining, with a computer, mineral composition models from a non-linear inversion of core or log elemental and mineral concentration data; and determining, with a computer, mineral concentrations for subsurface region from a linear inversion of core or geochemical log data from the subsurface region or analogous region and the mineral composition models.

6 Claims, 2 Drawing Sheets

(56) References Cited

U.S. PATENT DOCUMENTS

| | | | | |
|---|---|---|---|---|
| 2014/0214324 A1* | 7/2014 | Freedman | ............... | G01V 5/08 702/8 |
| 2015/0260034 A1 | 9/2015 | Herron et al. | | |
| 2016/0266275 A1* | 9/2016 | Akkurt | ................... | E21B 49/00 |

OTHER PUBLICATIONS

McCarty, D. K., et al. (2015) "Mineral-chemistry quantification and petrophysical calibration for multimineral evaluations: A nonlinear approach", AAPG Bulletin, v. 99, No. 7, pp. 1371-1397.

Freedman, E. et al. (2014) "New Method for Determining Mineralogy and Matrix Properties from Elemental Chemistry Measured by Gamma Ray Spectroscopy Logging Tools", SPE 170772, the SPE Annual Technical Conference and Exhibition, Amsterdam, The Netherlands, Oct. 27-29, 2014, pp. 599-608.

Galford, J., et al. (2009) "Field Test Results of a New Neutron Induced Gamma Ray Spectroscopy Geochemical Logging Tool", SPE 123992-MS, the SPE Annual Technical Conference and Exhibition, New Orleans, Louisiana, Sep. 24-27; pp. 1-22.

Herron, S.L., et al. (1996) "Quantitative Lithology: An Application for Open and Cased Hole Spectroscopy", SPWLA-1996-E, SPWLA 37$^{th}$ Annual Logging Symposium, Jun. 16-19, New Orleans, Louisiana; pp. 1-14.

Pemper, R., et al. (2006) "A New Pulsed Neutron Sonde for Derivation of Formation Lithology and Mineralogy", SPE-102770-MS, the SPE Annual Technical Conference and Exhibition, San Antonio, Texas, Sep. 24-27; pp. 1-13.

Theologou, P.N., et al.(2015) "Mineral-Chemistry Quantification and Petrophysical Calibration for Multi-Mineral Evaluations", AAPG/SEG International Conference & Exhibition, Melbourne, Australia, Sep. 13-16; 12 pages.

Xi, C. et al. (2014), "NPL-1: Identifying Lithology and Matrix for Unconventional Reservoir Based on Geochemical Elements Logs", EEE; Fifth International Conference on Intelligent Systems Design and Engineering Applications, pp. 528-532.

\* cited by examiner

METHOD OF ROCK MINERALOGY INTERPRETATION

CROSS-REFERENCE TO RELATED APPLICATION

This application claims the benefit of U.S. Provisional Patent Application 62/426,921 filed Nov. 28, 2016 entitled METHOD OF ROCK MINERALOGY INTERPRETATION, the entirety of which is incorporated by reference herein

TECHNOLOGICAL FIELD

Exemplary embodiments described herein pertain to the production of oil or gas (hydrocarbons) and geophysical prospecting. More specifically, exemplary embodiments described herein pertain to a method to interpret and quantify mineral compositions and concentrations using core and/or log mineralogy data.

BACKGROUND

This section is intended to introduce various aspects of the art, which may be associated with exemplary embodiments of the present technological advancement. This discussion is believed to assist in providing a framework to facilitate a better understanding of particular aspects of the technological advancement. Accordingly, it should be understood that this section should be read in this light, and not necessarily as admissions of prior art.

Recent developments in geochemical logging technology allow rapid and continuous measurements of elemental concentrations using pulsed neutron spectroscopy logging tools. Quantification of minerals using geochemical logs is important in hydrocarbon exploration, development, and production to assess and evaluate basin thermal history, reservoir quality, and diagenesis. Mineralogy logs also provide continuous measurements of rock matrix mineral concentrations for seismic attribute modeling, formation evaluation, and geomechanical modeling. Many laboratory analysis methods and techniques have been developed to quantify rock minerals using core samples which are costly to acquire and are limited in quantity and reservoir coverage. Furthermore, coring and core analysis programs are often planned and executed in field exploration and early development phases and well logs become the main data source afterwards. Recent technological advancements of pulsed neutron induced gamma ray spectroscopy logging tools enable direct measurements of an expanded list of elements that make it possible to describe the full set of mineral assemblages in both reservoir and non-reservoir rocks. Accurate interpretation of geochemical well logs requires crucial core data calibration to establish links between elemental concentrations and mineral concentrations.

There are two types of mineral log interpretation methods in the industry, matrix inversion method and multi-mineral solver method. The matrix inversion method uses core databases that consist of laboratory measured mineral and elemental concentrations from core samples. Inversion algorithms transforming elemental concentrations to mineral concentrations within the databases are first established using numerical optimization models and methods. These core-derived inversion models are subsequently used to interpret mineral logs acquired from reservoirs and fields that are not necessarily represented by core samples within the databases. This is the case for most new exploration and frontier assets in which a few exploration wells may have been drilled and a limited amount of core data is available. This interpretation approach is adopted by all logging service companies and vendors (Freedman 2014, Herron 1996, and Pemper 2006). This method also has a disadvantage that logging vendors have only limited access to core data that are available in public domain. A multi-mineral solver method is a whole rock based approach that does not require availability of large core mineralogy databases. The whole rock analysis method quantifies properties of rock matrix and fluids simultaneously using core and log data. The multi-mineral solver formulation entails that geochemical and conventional logs are combined to form a set of log response equations with matrix mineral concentrations and pore fluid volumes as unknowns. It is required that end member properties of matrix components and fluids as well as log responses be known or assumed. A linear inversion solver is applied to solve for mineral concentrations and fluid saturations. The process is often iterated manually to achieve convergence criteria (Galford 2009, Colson, 1989). Both methods do not address the challenges that chemical compositions of minerals are often not known and exhibit variations as results of deposition environments and diagenetic alterations and ion replacements across reservoirs or basins. The matrix inversion method assumes default chemical phases and compositions that are consistent with core samples within the databases. The multi-mineral method allows users to vary mineral compositions manually and it becomes a cumbersome task when the number of minerals is more than two. Multiple iterations are often required to converge to a reasonable solution.

Recent papers published by McCarty el al. (2015) describe the BestRock toolkit. BestRock uses a nonlinear approach to optimize whole-rock chemistry with mineralogy to calculate individual mineral structural formulas and trace element associations from which certain log response parameters can then be calculated. It provides refined quantities of the mineral species present in the formation, their structural formulas, and their predicted wireline log responses. FIG. 2 in McCarty et al. (2015) illustrates that the workflow interprets core data only and calculates end point log responses of the core minerals. The workflow is not designed to directly interpret well log data and it provides end point petrophysical parameters as input to multi-mineral log analysis.

McCarty et al. (2015) explains its optimization process within the non-linear solver under the heading "Optimization of Major Elements." The elemental concentration formulation appears to be a linear system of equations. McCarty et al. (2015) is not clear on how the non-linear solver is applied in solving the mass balance equations and what type of cost function is used in the optimization process.

Cheng et al. (2014) does not have any core or log data interpretation workflows.

U.S. Pat. No. 9,310,513 describes a downhole logging system in which raw radiation detector signals are collected and transformed into amplitude and frequency and energy distribution in unit of gamma ray count per unit of time per energy channel. The technology does not perform data post-processing after data is acquired downhole to generate rock elemental concentrations.

US Patent Publication 20150260034 describes a method for determining mineralogy models of arenites and arkoses by performing linear regressions using sum of calcium and magnesium dry weights. This method is limited to only two types of minerals using two elements and linear regressions US Patent Publication 20160266275 describes a method for quantifying minerals of rock samples using a joint inversion of two types of laboratory analytical data, DRIFT (diffuse reflectance infrared Fourier transform spectroscopy) and XRF (X-ray fluorescence), and it shows that it is capable of quantifying additional minerals than using DRIFT only.

U.S. Pat. No. 8,311,744 describes a method for estimating elemental yields and concentrations using a natural gamma ray spectrum, a fast neutron induced inelastic spectrum, and a thermal neutron induced capture spectrum and it performs spectral decomposition using a weighted sum of monoelemental spectral standards. It also uses a classifier or a classification system to receive elemental concentrations as input and to provide lithotypes as output.

SUMMARY

A method to interpret and quantify mineral compositions and concentrations, the method including: determining, with a computer, mineral composition models from a non-linear inversion of core or log elemental and mineral concentration data; and determining, with a computer, mineral concentrations for a subsurface region from a linear inversion of core or geochemical log data from the subsurface region or analogous subsurface region and the mineral composition models.

In the method, the determining the mineral composition models can include modeling mineral composition variations as constraints within the non-linear inversion.

In the method, the determining the mineral composition models can include using core elemental concentration data obtained from core samples taken from downhole or rock samples taken from outcrops.

In the method, the determining the mineral composition models can include using log elemental concentration data obtain from geochemical log data acquired using geochemical logging device.

In the method, the geochemical logging device can be a pulsed neutron induced gamma ray spectroscopy tool.

In the method, the non-linear inversion can solve for a number of atoms of an element in a mineral.

In the method, the linear inversion can solve for mineral dry weight fractions.

The method can further include generating, with a computer, field calibrated mineralogy logs from the mineral concentrations and the core or geochemical log data.

BRIEF DESCRIPTION OF THE DRAWINGS

While the present disclosure is susceptible to various modifications and alternative forms, specific example embodiments thereof have been shown in the drawings and are herein described in detail. It should be understood, however, that the description herein of specific example embodiments is not intended to limit the disclosure to the particular forms disclosed herein, but on the contrary, this disclosure is to cover all modifications and equivalents as defined by the appended claims. It should also be understood that the drawings are not necessarily to scale, emphasis instead being placed upon clearly illustrating principles of exemplary embodiments of the present invention. Moreover, certain dimensions may be exaggerated to help visually convey such principles.

DETAILED DESCRIPTION

Figure 1:
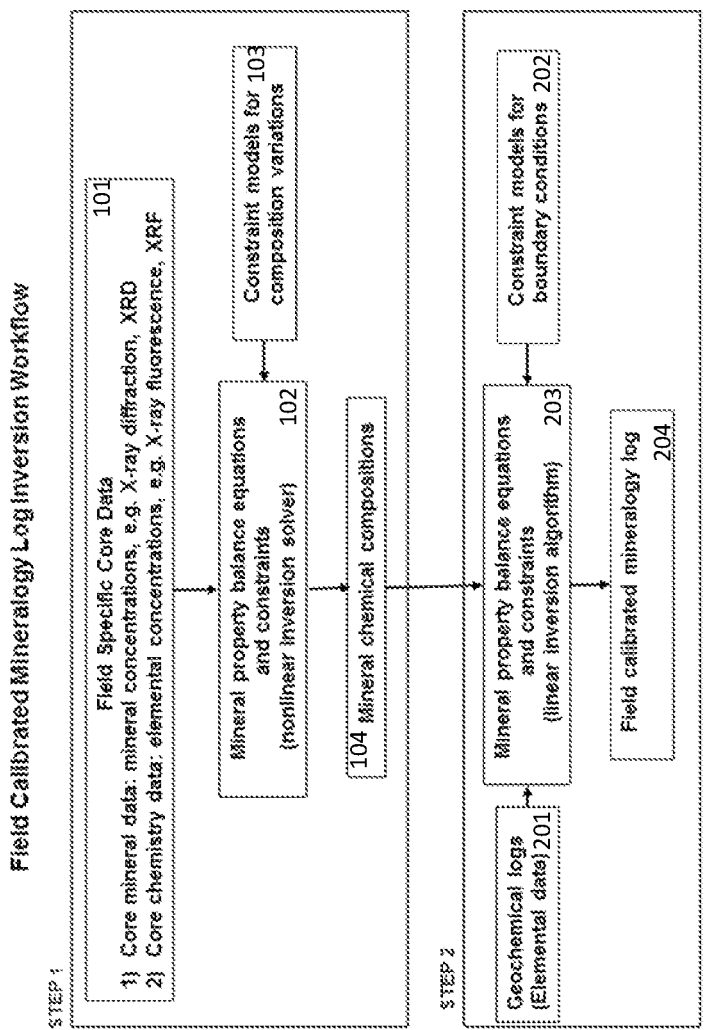
FIG. 1 illustrates an exemplary method embodying the present technological advancement.

Exemplary embodiments are described herein. However, to the extent that the following description is specific to a particular embodiment, this is intended to be for exemplary purposes only and simply provides a description of the exemplary embodiments. Accordingly, the invention is not limited to the specific embodiments described below, but rather, it includes all alternatives, modifications, and equivalents falling within the true spirit and scope of the appended claims.

The present technological advancement can provide a field calibrated mineral log inversion method. An embodiment of the present technological advancement can include the following two steps (corresponding to steps 1 and 2 in FIG. 1).

Firstly (step 1 of FIG. 1), the chemical compositions of minerals can be determined by solving nonlinear mineral property balance equations using core mineral data. These core samples can be taken from the fields or a close analog with similar lithology and depositional environment. Input parameters to the material balance equations are mineral concentrations from core mineral analysis such as X-ray diffractions (XRD) and elemental concentrations from core elemental analysis such as X-ray Fluorescence (XRF). Unknown variables are mineral chemical compositions represented as number of atoms. Constraints on variables to honor boundary conditions and other rules and restrictions are formulated and added in the solution equations. Sources of core data are not limited to XRF and XRD analyses. Similar analytical data from other core analysis techniques can also be used. As with any laboratory analytical techniques, true mineral phase and chemical compositions may not always be solvable, chemical compositions obtained in this step may therefore not always correspond to the true chemical compositions. However, these inversion results provide the best correlations possible between mineral and elemental concentrations obtained from core samples in laboratory analysis. Many mathematical inversion tools are available to solve non-linear problems. These include MATLAN MINCON; Tikhonov with 1-curve regularization, Truncated Singular Value Decomposition (SVD); Bounded Variable Least Square (BVLS), Tikhonov with Occam's regularization.

An objective of Step 1 is to define the mineral chemical composition using field specific core mineralogy data. In sub-step 101, field specific core data can be mineral concentrations from core mineral data obtained from X-ray diffraction (XRD) and elemental concentrations from core chemistry data obtained from X-ray fluorescence (XRF). Log elemental concentration data can be obtain from geochemical log data acquired using geochemical logging device, such as a pulsed neutron induced gamma ray spectroscopy tool. The elemental concentrations can be obtained from core samples taken from downhole or rock samples taken from outcrops. As an alternative, step 101 is to use log mineral data and log chemistry data as inputs A) and B) in sub-step 101.

Sub-step 102 uses a nonlinear solver to determine and then output mineral chemical compositions in sub-step 104. The elemental and mineral concentrations within a unit volume of rock are described in a mass balance equation in which total concentration of an element is the sum of elemental concentrations in minerals that contain the element within the rock matrix. Using mineral dry weights and elemental dry weighs, the equation can have the following form $$DW_{ELEM}^j = \sum_{i=0}^{nMIN} DW_{MIN}^i N_{ji} \frac{MW_j}{\sum_{k=1}^{nMIN} N_{ki}MW_k} \quad (1)$$

where $DW_{ELEM}^j$ is weight fraction of the jth element in the rock matrix, also called dry weight, and j=1 to J, $DW_{MIN}^i$ is weigh percent of the ith mineral in the rock matrix or dry weight, and l=1 to nMIN, $N_{ji}$ is the number of atoms of the jth element within the ith mineral, $MW_j$ is molecular weight of the jth mineral in g/mol, nMIN is the total number of minerals in the rock matrix, and $N_{ji}$, the number of atoms of jth element in ith mineral within Equation 1, is an unknown variable.

Since the unknown variable, $N_{ji}$ is contained in both the numerator and denominator in Equation 1, this is a nonlinear problem. In order to devise an inversion algorithm to solve for $N_{ji}$ for all elements within the system, Equation 1 is rewritten in matrix notation, $$DW_{ELEM} = M(X) \quad (2)$$

where $DW_{ELEM}$ is the elemental dry weight matrix and M(X) is the matrix with unknown atom quantities.

A cost function, $f(x)$, is defined along with constraint conditions and ranges for elements, $$f(x) = \|M(X) - DW_{ELEM}\|_2^2 \quad (3)$$

and $\sum_{l=0}^{L} X_l = H \quad (4)$ with $X_l \geq 0 \quad (5)$ where $X_l$ is number of atoms of element l within a mineral and H is atom sum constraint.

Sub-step 104 defines constraint models for composition variations. The atom number constraints can be defined for each mineral. For instance, glauconite molecules have chemical formula of (K, Na)(Fe3+, Al, Mg)2(Si, Al)4O10(OH)2. The elements in parentheses may substitute for one another as long as constraints on atom numbers are satisfied. A typical constraint for glauconite has the form of Fe+Al+Mg=2.

Another clay mineral, clinochlore, has chemical formula of (Mg, Fe 2+)5Al(Si3Al)O10(OH)8 and the corresponding constraint equation can be Mg+Fe=5.

The nonlinear inversion process in sub-step 102 is to solve for X by minimizing the function $f(x)$ while satisfying the constraint conditions. There are published nonlinear programming solvers that may be used for this type of problems. The performances of these toolkits vary in term of convergence speed and ability to reach a globally optimized solution. By solving for x, sub-step 102 determines mineral composition models from a non-linear inversion of core or log elemental and mineral concentration data (101), wherein such mineral chemical compositions are output in sub-step 103.

Secondly (step 2), the geochemical log data acquired in downhole pulsed neutron induced gamma ray spectroscopy tools can be analyzed using mineral chemical compositions defined in step 1. A complete set of mineral property balance equations can be established using elemental concentration log data and core-derived chemical compositions. The unknown variables are mineral concentrations at individual logging depths. Constraints on variables to honor boundary conditions and other rules and restrictions are formulated and added in the solution equations. These constraints improve the solution stability and uniqueness when the number of elements is less than the number of minerals and the system is underdetermined. The newly advanced geochemical logging technology measures and provides a comprehensive list of elemental concentrations. There are many reservoirs in which complex mineral types are often present. The potential underdetermined problems may also be optimized by combining and grouping minerals of similar properties such as Illite and Mica. This is often a good strategy to reduce the number of unknowns and lead to stable solutions. The results are mineral concentration log data that honor the core-derived chemical composition models.

Step 2 of the method, as illustrated in FIG. 1, is to apply the mineral composition solution, $N_{ji}$ to quantify mineral dry weight fractions, $DW_{MIN}^i$, using either log or core elemental dry weights as input. Sub-step 201 includes inputting the geochemical logs (elemental data) into a linear inversion solver. Alternatively, core elemental data could be used as an input when core mineralogy data is unknown. This would be applicable to interpreting core mineral data from depth intervals or offset wells where core elemental analysis is not completed or available. Step 202 inputs constraint models for boundary conditions into the linear solver. Sub-step 203 includes using the inputs from sub-steps 201 and 202, the mineral chemical compositions from sub-step 103, and defining a mass balance equation (6) similar to Equation 1 to determine field calibrated mineralogy logs from derived mineral concentration, and outputting the field calibrated mineralogy logs in sub-step 204.

$$DW_{ELEM}^j = \sum_{i=0}^{nMIN} DW_{MIN}^i N_{ji} \frac{MW_j}{\sum_{k=1}^{nMIN} N_{ki}MW_k} \quad (6)$$

The unknowns are mineral dry weight fractions, $DW_{MIN}^i$.

Equation 6 describes a linear problem. Rewriting Equation 6 into matrix notation yields, $$DW_{ELEM} = M(X) \quad (7)$$

where $DW_{ELEM}$ is the elemental dry weight matrix at each logging depth and M(X) is the matrix containing unknown mineral concentrations, $DW_{MIN}^i$.

A cost function, $f(x)$, can be defined along with constraint conditions (sub-step 202) and ranges for mineral concentrations, $$f(x) = \|M(X) - DW_{ELEM}\|_2^2 \quad (3)$$

and $$\sum_{i=1}^{nMIN} DW_{MIN}^i \leq 1, DW_{MIN}^i > 0, DW_{MIN}^i < 1$$

The linear inversion algorithm may be used to solve for X by minimizing the function $f(x)$ while satisfying the constraint conditions. There are published linear programming solvers that may be used for this type of problems. The performances of these toolkits vary in term of convergence speed and ability to reach a globally optimized solution.

The present technological advancement has been successfully benchmarked using multiple sets of core data from siliciclastic and carbonate fields as well as geochemical logs. The results are significantly better than existing methods.

The field calibrated mineralogy log from sub-step 204 can be used in hydrocarbon management to assess and evaluate basin thermal history, reservoir quality, and diagenesis. As used herein, hydrocarbon management includes hydrocarbon extraction, hydrocarbon production, hydrocarbon exploration, identifying potential hydrocarbon resources, identifying well locations, determining well injection and/or extraction rates, identifying reservoir connectivity, acquiring, disposing of and/or abandoning hydrocarbon resources, reviewing prior hydrocarbon management decisions, and any other hydrocarbon-related acts or activities.

Figure 2:
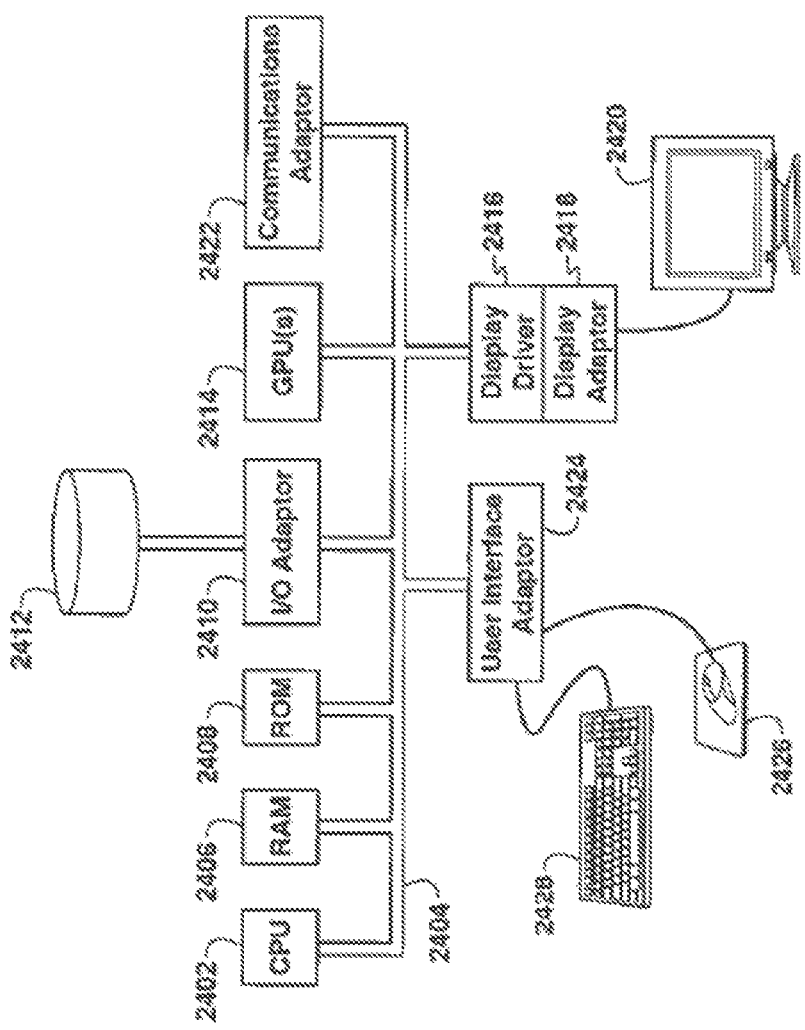
FIG. 2 illustrates an exemplary computer system for implementing embodiments of the present technological advancement.

FIG. 2 is a block diagram of a computer system 2400 that can be used to execute the present techniques. A central processing unit (CPU) 2402 is coupled to system bus 2404. The CPU 2402 may be any general-purpose CPU, although other types of architectures of CPU 2402 (or other components of exemplary system 2400) may be used as long as CPU 2402 (and other components of system 2400) supports the operations as described herein. Those of ordinary skill in the art will appreciate that, while only a single CPU 2402 is shown in FIG. 2, additional CPUs may be present. Moreover, the computer system 2400 may comprise a networked multi-processor computer system that may include a hybrid parallel CPU/GPU system. The CPU 402 may execute the various logical instructions according to various teachings disclosed herein. For example, the CPU 2402 may execute machine-level instructions for performing processing according to the operational flow described.

The computer system 2400 may also include computer components such as nontransitory, computer-readable media. Examples of computer-readable media include a random access memory (RAM) 2406, which may be SRAM, DRAM, SDRAM, or the like. The computer system 2400 may also include additional non-transitory, computer-readable media such as a read-only memory (ROM) 2408, which may be PROM, EPROM, EEPROM, or the like. RAM 2406 and ROM 2408 hold user and system data and programs, as is known in the art. The computer system 2400 may also include an input/output (I/O) adapter 2410, a communications adapter 2422, a user interface adapter 2424, and a display adapter 2418.

The I/O adapter 2410 may connect additional non-transitory, computer-readable media such as a storage device(s) 2412, including, for example, a hard drive, a compact disc (CD) drive, a floppy disk drive, a tape drive, and the like to computer system 2400. The storage device(s) may be used when RAM 2406 is insufficient for the memory requirements associated with storing data for operations of the present techniques. The data storage of the computer system 2400 may be used for storing information and/or other data used or generated as disclosed herein. For example, storage device(s) 2412 may be used to store configuration information or additional plug-ins in accordance with the present techniques. Further, user interface adapter 2424 couples user input devices, such as a keyboard 2428, a pointing device 2426 and/or output devices to the computer system 400. The display adapter 2418 is driven by the CPU 2402 to control the display on a display device 2420 to, for example, present information to the user regarding available plug-ins.

The architecture of system 2400 may be varied as desired. For example, any suitable processor-based device may be used, including without limitation personal computers, laptop computers, computer workstations, and multi-processor servers. Moreover, the present technological advancement may be implemented on application specific integrated circuits (ASICs) or very large scale integrated (VLSI) circuits. In fact, persons of ordinary skill in the art may use any number of suitable hardware structures capable of executing logical operations according to the present technological advancement. The term "processing circuit" encompasses a hardware processor (such as those found in the hardware devices noted above), ASICs, and VLSI circuits. Input data to the computer system 2400 may include various plug-ins and library files. Input data may additionally include configuration information.

The present techniques may be susceptible to various modifications and alternative forms, and the examples discussed above have been shown only by way of example. However, the present techniques are not intended to be limited to the particular examples disclosed herein. Indeed, the present techniques include all alternatives, modifications, and equivalents falling within the spirit and scope of the appended claims.

REFERENCES

The following references are hereby incorporated by reference in their entirety:

Cheng et al, 2014, "NPL-1: Identifying Lithology and Matrix for Unconventional Reservoir Based on Geochemical Elements Logs", EEE; Fifth International Conference on Intelligent Systems Design and Engineering Applications;

Freedman, E. et al., 2014, "New method for determining mineralogy and matrix properties from elemental chemistry measurement by gamma ray spectroscopy logging tools", SPE 170772, the SPE Annual Technical Conference and Exhibition, Amsterdam, The Netherlands, October 27-29;

Herron, S. L., and Herron, M. M., 1996, "Quantitative lithology: an application for open and cased hole spectroscopy", Paper E, SPWLA $37^{th}$ Annual Logging Symposium, June 16-19;

Pemper, R., et al., 2006, "A new pulsed neutron sonde for derivation of formation lithology and mineralogy", SPE 102770, the SPE Annual Technical Conference and Exhibition, San Antonio, Tex., September 24-27;

Galford, J., et al., 2009, "Field test results of a new neutron-induced gamma-ray spectroscopy geochemical logging tool", SPE 123992, the SPE Annual Technical Conference and Exhibition, New Orleans, La., September 24-27;

Colson, J. L., et al., 1989, "Applications using geochemical logs", SPE 17963, the SPE Middle East Oil Technical Conference and Exhibition, Manama, Bahrain, March 11-14;

Douglas K. McCarty, Paul N. Theologou, Timothy B. Fischer, Arkadiusz Derkowski, M. Rebecca Stokes, and Ann Ollila, 2015, "Mineral-chemistry quantification and petrophysical calibration for multimineral evaluation, a non-linear approach", AAPG Bulletin, v. 99, no. 7, pp. 1371-1397;

Paul N. Theologou, Douglas K. McCarty, Timothy B. Fischer, Arkadiusz Derkowski, M. Rebecca Stokes, and Ann Ollila, 2015, "Mineral-chemistry quantification and petrophysical calibration for multi-mineral evaluation", AAPG/SEG International Conference & Exhibitionm Melbourne, Australia, September 13-16; and U.S. Pat. No. 9,310,513, 20150260034, 20160266275, and U.S. Pat. No. 8,311,744.

What is claimed is:

1. A method to interpret and quantify mineral compositions and concentrations in a subsurface region, the method comprising:
   determining, with a computer, mineral composition models from a non-linear inversion of elemental and mineral concentration data obtained from elemental and mineral analysis of one or more core samples, wherein said determining mineral composition models comprises determining the number of atoms of each element within each mineral of the one or more core samples;
   determining, with a computer, mineral concentrations for the subsurface region from a linear inversion of core or geochemical log data from the subsurface region or analogous subsurface region and the mineral composition models, wherein said determining mineral concentrations comprises determining the mineral dry weight fractions as a function of logging depth, using as input the determined mineral composition models comprising number of atoms of each element within each mineral;
   generating, with a computer, field calibrated mineralogy logs from the determined mineral concentrations and said elemental and mineral concentration data obtained from elemental and mineral analysis of said one or more core samples; and
   managing hydrocarbons in the subsurface region using the field calibrated mineralogy logs.

2. The method of claim 1, wherein the determining the mineral composition models includes modeling mineral composition variations as constraints within the non-linear inversion.

3. The method of claim 1, wherein the determining the mineral composition models includes using core elemental concentration data obtained from core samples taken from downhole or rock samples taken from outcrops.

4. The method of claim 1, wherein the determining the mineral composition models includes using log elemental concentration data obtain from geochemical log data acquired using geochemical logging device.

5. The method of claim 4, wherein the geochemical logging device is a pulsed neutron induced gamma ray spectroscopy tool.

6. The method of claim 1, wherein managing hydrocarbons comprises extracting hydrocarbons from the subsurface formation.

* * * * *